US00PP32551P2

(12) United States Plant Patent
Hoof

(10) Patent No.: US PP32,551 P2
(45) Date of Patent: Dec. 1, 2020

(54) ***HYDRANGEA* PLANT NAMED 'LITTLE ALF'**

(50) Latin Name: *Hydrangea paniculata*
Varietal Denomination: Little Alf

(71) Applicant: Ralph Matheus Hoof, Zevenaar (NL)

(72) Inventor: Ralph Matheus Hoof, Zevenaar (NL)

(73) Assignee: VAN VLIET NEW PLANTS B.V., Stroe (NL)

( * ) Notice: Subject to any disclaimer, the term of this patent is extended or adjusted under 35 U.S.C. 154(b) by 0 days.

(21) Appl. No.: 16/873,413

(22) Filed: Apr. 9, 2020

(30) Foreign Application Priority Data

Jul. 16, 2019 (QZ) ..... PBR 20191716

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of *Hydrangea paniculata* plant named 'Little Alf' that is characterized but its compact plant habit, its leaves that are small in size, its dense panicles of sterile and fertile flowers, its flowering stems that are greyed-purple in color, and its inflorescences with sterile sepals that are white in color.

2 Drawing Sheets

Botanical classification: *Hydrangea paniculata.*
Varietal denomination: 'Little Alf'.

CROSS-REFERENCE TO A RELATED APPLICATION

This application claims priority to European Community Plant Variety Office (CPVO) Plant Breeder's Rights Application No. 2019/1716 filed on Jul. 16, 2019 under 35 U.S.C. 119(f), the entire contents of which is incorporated by reference herein.

BACKGROUND OF THE INVENTION

The present invention relates to a new and distinct cultivar of *Hydrangea paniculata* and will be referred to hereafter by its cultivar name, 'Little Alf'. 'Little Alf' represents a new *Hydrangea*, a perennial shrub grown for landscape use and as a potted plant.

'Little Alf' was derived from a breeding program conducted by the Inventor at a nursery in Zevenaar, The Netherlands. The objective of the breeding program is to select new cultivars of *Hydrangea* with compact plant habits combined with other desirable characteristics.

The new cultivar arose from a cross made by the Inventor in Zevenaar, The Netherlands in August of 2015 between *Hydrangea* 'Grandiflora' (not patented) as the female parent and *Hydrangea* 'Dharuma' (not patented) as the male parent. The Inventor selected 'Little Alf' as a single unique plant amongst the seedlings that resulted from the above cross in August of 2017.

Asexual propagation of the new cultivar was first accomplished by softwood stem cuttings by the Inventor in September of 2017 in Zevenaar, The Netherlands. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Little Alf' as a unique cultivar of *Hydrangea.*

1. 'Little Alf' exhibits a compact plant habit.
2. 'Little Alf' exhibits leaves that are small in size.
3. 'Little Alf' exhibits dense panicles of sterile and fertile flowers.
4. 'Little Alf' exhibits flowering stems that are greyed-purple in color.
5. 'Little Alf' exhibits inflorescences with sterile sepals that are white in color.

The seed parent of 'Little Alf' differs from 'Little Alf' in having longer lateral branches resulting in a less compact plant habit. The pollen parent of 'Little Alf' differs from 'Little Alf' in having a less compact plant habit, leaves that are larger in size and inflorescences that are less dense. 'Little Alf' can be most closely compared to the *Hydrangea paniculata* cultivars 'Jane' (U.S. Plant Pat. No. 22,330) and 'Bokraflame' (U.S. Plant Pat. No. 22,111). 'Jane' is similar to 'Little Alf' in having a compact plant habit and inflorescences with sterile and fertile flowers. 'Jane' differs from 'Little Alf' in having a slightly taller plant height, leaves that are larger in size, stems that are green to grey-orange in color and sepals that are light yellow-green in color. 'Bokraflame' is similar to 'Little Alf' in having a compact plant habit. 'Bokraflame' differs from 'Little Alf' in having inflorescences that are less rounded in shape, sterile flowers that mature to a deep grey-red color and a less compact plant habit.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website listings by Sklep Internetowy Z Rzadkimi I Pospolitymi Roslinami, KOKAUDZÉTAVA BALTEZERS, Newplants (van Vliet New Plants), floraplanet, Morton nurseries, Tully nurseries, E-Clematis, gardeners dream, Allegro plants, and Kurowski.

BRIEF DESCRIPTION OF THE DRAWINGS

The accompanying colored photographs illustrate the overall appearance and distinct characteristics of the new *Hydrangea*. The photographs were taken of a two-year-old plant of 'Little Alf' as field grown outdoors in Stroe, The Netherlands and placed in a 23-cm container for the photographs.

The photograph in FIG. 1 provides a side view of the plant habit of 'Little Alf' in bloom.

Figure 1:
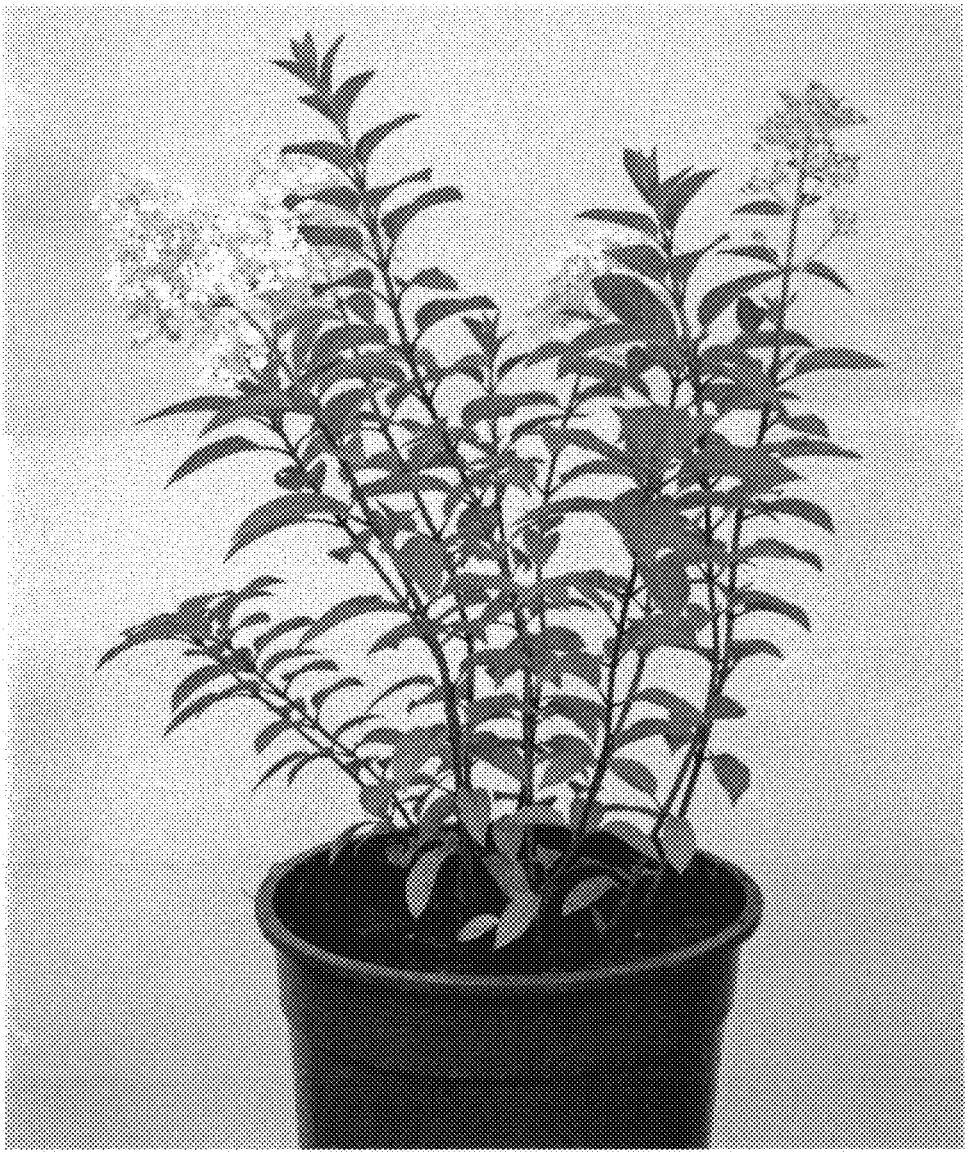
Figure 2:
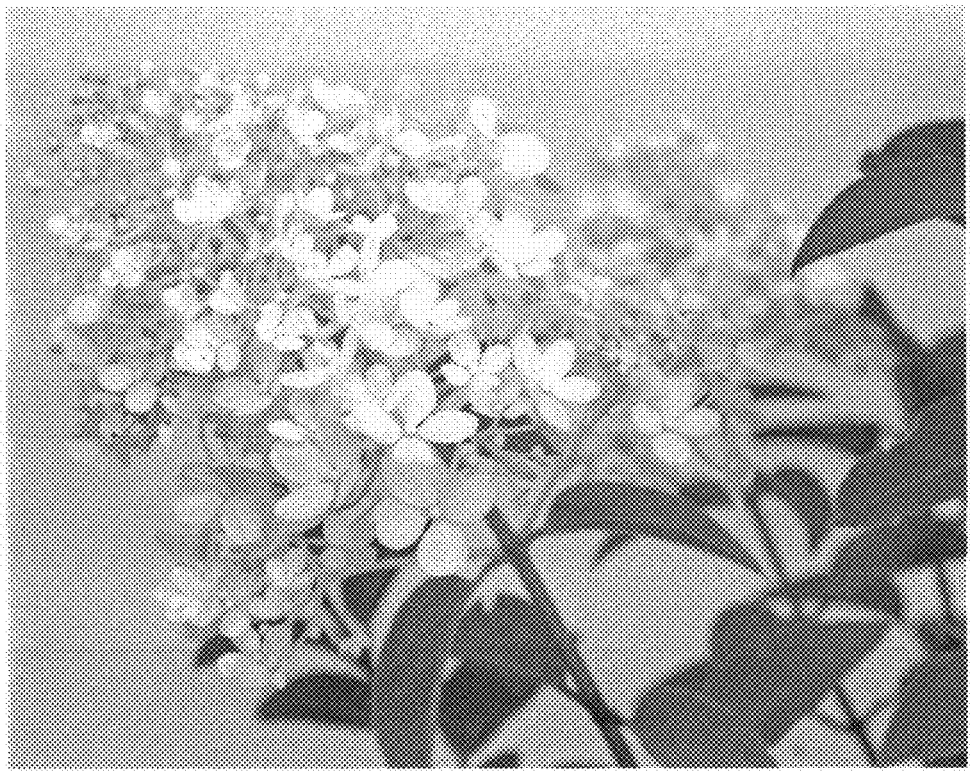

The photograph in FIG. 2 provides a close-up view of an inflorescence of 'Little Alf'.

Figure 3:
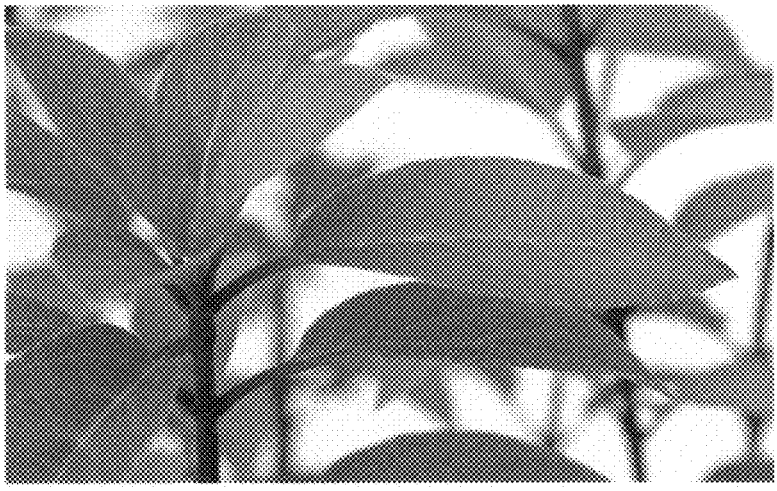

The photograph in FIG. 3 provides a close-up view of the foliage of 'Little Alf'.

The colors in the photographs are as close as possible with the photographic and printing technology utilized and the color values cited in the detailed botanical description accurately describe the colors of the new *Hydrangea*.

BOTANICAL DESCRIPTION OF THE PLANT

The following is a detailed description of two-year-old plants of 'Little Alf' as field grown in Stroe, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

- *Blooming period*.—Approximately 5 weeks from mid to late summer in The Netherlands.
- *Plant type*.—Deciduous shrub, panicle type *Hydrangea*.
- *Plant habit*.—Compact, broadly upright.
- *Height and spread*.—Reaches 50 cm in height and spread as a two-year old plant in the landscape.
- *Hardiness*.—At least in U.S.D.A. Zones 5 to 9.
- *Diseases and pests*.—No susceptibility and resistance to diseases or pests has been observed.
- *Root description*.—Fine, fibrous and dense, NN155A and 164A in color.
- *Propagation*.—Softwood stem cuttings.
- *Root development*.—An average of 30 days for root initiation with a young rooted plant produced in an average of 3 months.
- *Growth rate and vigor*.—Low to moderate.

Stem description:

- *Stem shape*.—Rounded.
- *Stem strength*.—Strong.
- *Stem color*.—Young; N148A with lenticels 193C, mature; 178A, bark; 200D.
- *Stem size*.—Average of 39.1 cm in length and 3.5 mm in diameter.
- *Stem surface*.—Moderately covered with lenticels an average of 1 mm in length and 0.3 mm in diameter, 159B in color, young stems are very sparsely covered with short adpressed hairs; average of 0.2 mm in length and too small to measure color.
- *Stem aspect*.—Upright, average angle of 25° to vertical.
- *Internode length*.—An average of 3.1 cm.
- *Branching*.—Freely branching with an average of 12 lateral branches.

Foliage description:

- *Leaf shape*.—Ovate.
- *Leaf arrangement*.—Opposite.
- *Leaf division*.—Simple.
- *Leaf base*.—Obtuse to truncate.
- *Leaf apex*.—Acute to slightly apiculate.
- *Leaf margins*.—Serrate.
- *Leaf venation*.—Pinnate, color; upper surface 152B, lower surface 195B.
- *Leaf size*.—An average of 6 cm in length and 3 cm in width.
- *Leaf attachment*.—Petiolate.
- *Leaf number*.—An average of 22 per lateral stem.
- *Leaf surface*.—Both surfaces matte and sparsely to moderately pubescent with very short adpressed strigose hairs; an average of 0.3 mm in length, color too small and too sparsely present to be measured.
- *Leaf color*.—Young upper surface; 143B, young lower surface; 144B, mature upper surface; 143A, mature lower surface; 138B.
- *Petioles*.—An average of 1.5 cm in length and 2 mm in diameter, upper surface 183A in color, lower surface 177D in color, slightly glossy, glabrous, smooth, margins sparsely covered with very short hairs; average length 0.2 mm, color too small and too sparsely present to be measured.

Inflorescence description:

- *Inflorescence type*.—Terminal conical compact panicle, comprised of sterile flowers and fertile flowers.
- *Lastingness of inflorescence*.—Sterile flowers; persistent for an average of 6 weeks, fertile flowers; self-cleaning, an average of 5 days.
- *Inflorescence number*.—One per lateral stem.
- *Inflorescence size*.—An average of 11.2 cm in height and 10 cm in diameter.
- *Flower number*.—An average of 300 sterile flowers and 400 fertile flowers per panicle.
- *Flower fragrance*.—Faint, sweet and pleasant.
- *Flower aspect*.—Sterile flowers; upright to outward, fertile flowers; upright to outward.
- *Flower size*.—Sterile flowers; up to 1.8 cm in diameter and 5 mm in depth, fertile flowers; an average of 5 mm in diameter and 2.5 mm in depth.
- *Flower type*.—Sterile flowers; rotate, fertile flowers; rotate, petals drop when mature.
- *Flower buds*.—Sterile flowers; an average of 5 mm in length and 6 mm in diameter, cup-shaped, 145B in color, fertile flowers; an average of 2.5 mm in length and 2 mm in diameter, obovate in shape, 157D in color, immature calyx 157A in color.

*Peduncles*.—Primary peduncles; strong, flattened oval in shape, moderate in strength, an average of 2.5 cm in length and 3 mm in width. secondary peduncles 2 cm in length and 2 mm in width, 157D in color, surface moderately covered with a thin pubescence; average of 0.2 mm in length, 157D in color.

*Pedicels*.—Sterile flowers; moderate strength, an average of 1.2 cm in length and 1 mm in width, 157D in color, held in an average angle of 50° to main peduncle, surface is matte, densely covered with thin pubescence; average of 0.3 mm in length, 155A in color, fertile flowers; moderate strength, an average of 4 mm in length, 1 mm in diameter, held in an average angle of 20°, 157D in color, surface is matte, sparsely to moderately covered with a thin pubescence; average of 0.2 mm in length, 157D in color.

*Petals*.—Sterile flowers; average of 5, rotate, ovate to slightly concave in shape, acute apex, cuneate base, entire margins, 2 mm in length, 1 mm in width, upper surface glabrous and slightly glossy, lower surface glabrous and matte, color when opening and fully open upper and lower surface NN155D, fertile flowers; average of 5, rotate, ovate to moderately concave in shape, acute apex, cuneate base, entire margins, 2 mm in length and 1 mm in width, upper surface is glabrous and slightly glossy, lower surface glabrous and matte, color when opening and fully open upper and lower surface NN155D.

*Sepals*.—Sterile flowers; 4 (occasionally 5), rotate, obovate to broadly elliptic in shape, apex is undeeply emarginate to obtuse, base is cuneate, entire margins that are non-undulate, 9 mm in length, 6.5 mm in width, both surfaces glabrous and matte, color; when opening upper surface 157B, when opening lower surface 157B to 157C, when fully open upper and lower surface NN155B, fertile flowers; average of 5, rotate, short deltoid in shape, broadly cuneate apex, broadly cuneate base, entire margins, 1 mm in length and width, both surfaces glabrous and matte, color; when opening and fully opening upper and lower surface a color between 145D and 157A.

Reproductive organs:

*Gynoecium*.—Sterile flowers; pistil; 1, average of 1 mm in length, stigma; club-shaped, 155A in color, style; 0.5 mm in length, 157A in color, ovary; 150D in color, fertile flowers; 3 pistils, an average of 1 mm in length, stigma; club-shaped and 155A in color, style; 0.5 mm in length, 157A in color, ovary is 145D in color.

*Androecium*.—Sterile flowers; an average of 8 stamens, filaments; an average of 1.5 mm in length and 155A in color, anthers; double broad oblong in shape, an average of 0.5 mm in length and 158D in color, pollen; low in quantity and 158D in color, fertile flowers; an average of 10 stamens, filaments; an average of 2 mm in length and NN155A in color, anthers; double broad oblong in shape, an average of 0.5 mm in length and 158D in color, pollen; low in quantity and 158D in color.

*Fruit and seed*.—None observed to date.

It is claimed:

1. A new and distinct cultivar of *Hydrangea* plant named 'Little Alf' substantially as herein illustrated and described.

* * * * *